(12) United States Patent
Paparizos et al.

(10) Patent No.: US 7,348,291 B2
(45) Date of Patent: *Mar. 25, 2008

(54) CATALYST FOR THE MANUFACTURE OF ACRYLONITRILE

(75) Inventors: Christos Paparizos, Willoughby, OH (US); Stephen C. Jevne, Wheaton, IL (US); Michael J. Seely, Naperville, IL (US)

(73) Assignee: Ineos USA LLC, Lisle, IL (US)

(*) Notice: Subject to any disclaimer, the term of this patent is extended or adjusted under 35 U.S.C. 154(b) by 539 days.

This patent is subject to a terminal disclaimer.

(21) Appl. No.: 10/717,846

(22) Filed: Nov. 19, 2003

(65) Prior Publication Data

US 2004/0110978 A1 Jun. 10, 2004

Related U.S. Application Data

(60) Provisional application No. 60/430,162, filed on Dec. 2, 2002.

(51) Int. Cl.
*B01J 23/28* (2006.01)
*C07C 253/24* (2006.01)

(52) U.S. Cl. ..................... 502/304; 558/321
(58) Field of Classification Search ............... 502/241, 502/215, 304; 558/319, 321
See application file for complete search history.

(56) References Cited

U.S. PATENT DOCUMENTS

| | | | |
|---|---|---|---|
| 4,414,133 A | 11/1983 | Otake et al. | 502/179 |
| 4,746,753 A | 5/1988 | Brazdil, Jr. et al. | 558/324 |
| 4,939,286 A | 7/1990 | Brazdil et al. | 558/324 |
| 5,093,299 A | 3/1992 | Suresh et al. | 502/212 |
| 5,134,105 A | 7/1992 | Paparizos et al. | 502/205 |
| 5,175,334 A | 12/1992 | Suresh et al. | 558/324 |
| 5,212,137 A | 5/1993 | Suresh et al. | 502/212 |
| 5,235,088 A | 8/1993 | Paparizos et al. | 558/324 |
| 5,364,825 A | 11/1994 | Neumann et al. | 502/311 |
| 5,583,084 A | 12/1996 | Martin et al. | 502/211 |
| 5,583,086 A | 12/1996 | Tenten et al. | 502/249 |
| 5,658,842 A | 8/1997 | Midorikawa et al. | 502/314 |
| 5,663,113 A | 9/1997 | Midorikawa et al. | 502/314 |
| 5,780,664 A | 7/1998 | Aoki | 558/323 |
| 5,808,143 A | 9/1998 | Karrer et al. | 562/407 |
| 5,834,394 A | 11/1998 | Chen et al. | 502/302 |
| 5,840,648 A | 11/1998 | Suresh et al. | 502/306 |
| 6,143,690 A | 11/2000 | Komada et al. | 502/211 |
| 6,420,307 B1 | 7/2002 | Wu et al. | 502/302 |
| 6,458,742 B1 | 10/2002 | Paparizos et al. | 502/304 |
| 7,071,140 B2* | 7/2006 | Paparizos et al. | 502/215 |

FOREIGN PATENT DOCUMENTS

| | | |
|---|---|---|
| CN | 1114915 A | 1/1996 |
| CN | 1230459 A | 10/1999 |
| CN | 1310046 A | 2/2000 |
| CN | 1287882 A | 3/2001 |
| CN | 1302690 A | 7/2001 |
| CN | 1310172 A | 8/2001 |
| EP | 1223162 A1 | 7/2002 |
| JP | 07047272 A | 2/1995 |
| JP | 020045696 | 2/2002 |
| WO | WO0114057 A | 3/2001 |
| WO | WO03033139 A1 | 9/2002 |

* cited by examiner

*Primary Examiner*—James O. Wilson
*Assistant Examiner*—Ebenezer Sackey
(74) *Attorney, Agent, or Firm*—David P. Yusko

(57) ABSTRACT

A catalyst comprising a complex of catalytic oxides comprising potassium, cesium, cerium, chromium, cobalt, nickel, iron, bismuth, molybdenum, wherein the relative ratios of these elements is represented by the following general formula $$A_aK_bCs_cCe_dCr_eCo_fNi_gX_hFe_iBi_jMo_{12}O_x$$

wherein
A is Rb, Na, Li, Tl, or mixtures thereof,
X is P, Sb, Te, B, Ge, W, Ca, Mg, a rare earth element, or mixtures thereof,
a is 0 to about 1,
b is about 0.01 to about 1,
c is about 0.01 to about 1,
d is about 0.01 to about 3,
e is about 0.01 to about 2,
f is about 0.01 to about 10,
g is about 0.1 to about 10,
h is 0 to about 4,
i is about 0.1 to about 4,
j is about 0.05 to about 4,
x is a number determined by the valence requirements of the other elements present,
and wherein the catalyst is substantially free of manganese and zinc. The catalyst is useful in processes for the ammoxidation of an olefin selected from the group consisting of propylene, isobutylene or mixtures thereof, to acrylonitrile, methacrylonitrile and mixtures thereof, respectively.

21 Claims, No Drawings

CATALYST FOR THE MANUFACTURE OF ACRYLONITRILE

This application claims benefit of U.S. Provisional Patent Application Ser. No. 60/430,162 filed Dec. 2, 2002.

BACKGROUND OF THE INVENTION

1. Field of the Invention

The present invention relates to an improved catalyst for use in the ammoxidation of an unsaturated hydrocarbon to the corresponding unsaturated nitrile. In particular, the present invention is directed to an improved process and catalyst for the ammoxidation of propylene and/or isobutylene to acrylonitrile and/or methacrylonitrile, respectively. More specifically, the invention relates to a novel and improved ammoxidation catalyst comprising a complex of catalytic oxides of potassium, cesium, cerium, chromium, cobalt, nickel, iron, bismuth, and molybdenum, in the substantial absence of any of manganese, and zinc.

2. Description of the Prior Art

Catalysts containing oxides of iron, bismuth and molybdenum, promoted with suitable elements, have long been used for the conversion of propylene at elevated temperatures in the presence of ammonia and oxygen (usually in the form of air) to manufacture acrylonitrile. In particular, Great Britain Patent 1436475; U.S. Pat. Nos. 4,766,232; 4,377,534; 4,040,978; 4,168,246; 5,223,469 and 4,863,891 are each directed to bismuth-molybdenum-iron catalysts which may be promoted with the Group II elements to produce acrylonitrile. In addition, U.S. Pat. No. 4,190,608 discloses similarly promoted bismuth-molybdenum-iron catalyst for oxidation of olefins. U.S. Pat. Nos. 5,093,299, 5,212,137, 5,658,842 and 5,834,394 are directed to bismuth-molybdenum promoted catalysts exhibiting high yields to acrylonitrile.

An object of the instant invention is a novel catalyst comprising a unique combination of promoters offering better performance in the catalytic ammoxidation of propylene, isobutylene or mixtures thereof, to acrylonitrile, methacrylonitrile and mixtures thereof, respectively.

SUMMARY OF THE INVENTION

The present invention is directed to an improved catalyst and process for the ammoxidation of propylene and/or isobutylene to acrylonitrile and/or methacrylonitrile, respectively.

In one embodiment, the invention is catalyst comprising a complex of catalytic oxides comprising potassium, cesium, cerium, chromium, cobalt, nickel, iron, bismuth, molybdenum, wherein the relative ratios of these elements are represented by the following general formula:

$$A_a K_b Cs_c Ce_d Cr_e Co_f Ni_g X_h Fe_i Bi_j Mo_{12} O_x$$

wherein A is Rb, Na, Li, Tl, or mixtures thereof,
X is P, Sb, Te, B, Ge, W, Mg, a rare earth element, or mixtures thereof,
a is 0 to about 1,
b is about 0.01 to about 1,
c is about 0.01 to about 1,
d is about 0.01 to about 3,
e is about 0.01 to about 2,
f is about 0.01 to about 10,
g is about 0.1 to about 10,
h is 0 to about 3,
i is about 0.1 to about 4,
j is about 0.05 to about 4,
x is a number determined by the valence requirements of the other elements present, and wherein the catalyst is substantially free of manganese and zinc.

The present invention is directed to an ammoxidation catalyst comprising a complex a complex of catalytic oxides comprising potassium, cesium, cerium, chromium, cobalt, nickel, iron, bismuth, molybdenum, wherein the relative ratios of these elements are represented by the following general formula:

$$A_a K_b Cs_c Ce_d Cr_e Co_f Ni_g X_h Fe_i Bi_j Mo_{12} O_x$$

wherein A is Rb, Na, Li, Tl, or mixtures thereof,
X is P, Sb, Te, B, Ge, W, Ca, Mg, a rare earth element or mixtures thereof,
a is 0 to about 1,
b is about 0.01 to about 1,
c is about 0.01 to about 1,
d is about 0.01 to about 3,
e is about 0.01 to about 2,
f is about 0.01 to about 10,
g is about 0.1 to about 10,
h is 0 to about 4,
i is about 0.1 to about 4,
j is about 0.05 to about 4,
x is a number determined by the valence requirements of the other elements present, and wherein the catalyst is substantially free of manganese and zinc.

The subscripts in the above formula represent the potential ranges for the ratios of the individual elements with respect to molybdenum. One skilled in the art will know and appreciate that for any catalyst composition, the total quantity of the metallic elements, in view of their respective oxidation states, must be maintained in balance with molybdenum.

In one embodiment, the amount (on an atomic basis) of cerium plus chromium is greater than the amount of bismuth (i.e. "b"+"c" is greater than "g"). In another embodiment, the amount (on an atomic basis) of cerium is greater than the amount of chromium (i.e. "b" is greater than "c"). In other embodiments, "a" is about 0.05 to about 0.5, "b" is about 0.01 to about 0.3, "c" is about 0.01 to about 0.3, "d" is about 0.01 to about 3, "f+g" is about 4 to about 10, "h" is 0 to about 3, "i" is about 1 to about 3, and "j" is about 0.1 to about 2.

The basic catalyst composition described herein is a complex of catalytic oxides of potassium, cesium, cerium, chromium, cobalt, nickel, iron, bismuth, and molybdenum. Except for specifically excluded elements, other elements or promoters may be included. In one embodiment, the catalyst may include one or more of rubidium, sodium, lithium, thallium, phosphorus, antimony, tellurium, boron, germanium, tungsten, calcium, magnesium, and a rare earth element (defined herein as any one of La, Pr, Nd, Pm, Sm, Eu, Gd, Tb, Dy, Ho, Er, Tm, or Yb). In yet another embodiment, the catalyst contains a small amount of phosphorus, (i.e. "X" is at least P and "h" is greater than zero), which has a beneficial effect on the attrition resistance of the catalyst. In yet another embodiment, the catalyst contains magnesium (i.e. "X" is at least Mg and "h" is greater than zero); in this embodiment, preferably "h" is about 1 to about 3. In yet another embodiment, the catalyst is substantially free of magnesium but contains at least one of the "X" elements (i.e.

"X" is at least one of P, Sb, Te, B, Ge, W, a rare earth element and "h" is greater than zero); in this embodiment, preferably "h" is about 0.1 to about 2. In yet another embodiment, the catalyst contains rubidium (i.e. "A" is at least Rb and "a" is greater than zero). In yet another embodiment, the catalyst is substantially free of rubidium. In yet another embodiment, the catalyst contains lithium (i.e. "A" is at least Li and "a" is greater than zero). In yet another embodiment, the catalyst contains lithium and the ratio of lithium to molybdenum is in the range of about 0.01:12 to about 1:12 (i.e. when "A" is Li alone, then "a" is about 0.1 to about 1). For mixed oxide catalyst systems comprising iron, bismuth and molybdenum used for the ammoxidation of propylene to acrylonitrile, the combination of cobalt and lithium as additional promoters, yields more total nitriles, e.g. acrylonitrile, acetonitrile and hydrogen cyanide (also referred to as formonitrile). In yet another embodiment, the catalyst is substantially free of strontium, and preferably contains no strontium. As used herein, "substantially free" with respect to any element, means the catalyst contains essentially none of that element.

Additionally, for the conversion of propylene, ammonia and oxygen to acrylonitrile, the inclusion of certain elements have been identified as being detrimental to obtaining a catalyst with improved acrylonitrile yields. These are manganese and zinc. The inclusion of manganese and zinc in the catalyst results in a less active catalyst and provides lower yields of acrylonitrile. As such the catalyst of the instant invention is described as being substantially free of manganese and zinc. As used herein, "substantially free", with respect to manganese, means having atomic ratio with respect to molybdenum of less than 0.1:12. As used herein, "substantially free", with respect to zinc means having atomic ratio with respect to molybdenum of less than 1:12. Preferably, the catalysts contain no manganese and/or zinc.

The catalyst of the present invention may be used either supported or unsupported (i.e. the catalyst may comprise a support). If a support is used, the support is typically mixed with the metal oxides that comprise the catalyst, or the support material may be impregnated with the metal oxides. Suitable supports are silica, alumina, zirconium, titania, or mixtures thereof A support typically serves as a binder for the catalyst resulting in a harder and more attrition resistant catalyst. However, for commercial applications, an appropriate blend of both the active phase (i.e. the complex of catalytic oxides described above) and the support is crucial to obtain an acceptable activity and hardness (attrition resistance) for the catalyst. Directionally, any increase in the active phase increases the activity of the catalyst, but decreases the hardness of the catalyst. Typically, the support comprises between 40 and 60 weight percent of the supported catalyst. In one embodiment of this invention, the support may comprise as little as about 30 weight percent of the supported catalyst. In another embodiment of this invention, the support may comprise as much as about 70 weight percent of the supported catalyst.

In one embodiment the catalyst is supported using a silica sol. If the average colloidal particle diameter of said silica sol is too small, the surface area of the manufactured catalyst will be increased and the catalyst will exhibit reduced selectivity. If the colloidal particle diameter is too large, the manufactured catalyst will have poor anti-abrasion strength. Typically, the average colloidal particle diameter of the silica sol is between about 15 nm and about 50 nm. In one embodiment of this invention, the average colloidal particle diameter of the silica sol is about 10 nm and can be as low as about 8 nm. In another embodiment of this invention, the average colloidal particle diameter of the silica sol is about 100 nm. In another embodiment of this invention, the average colloidal particle diameter of the silica sol is about 20 nm.

The catalysts of the present invention may be prepared by any of the numerous methods of catalyst preparation, which are known to those of skill in the art. For example, the catalyst may be manufactured by co-precipitating the various ingredients. The co-precipitating mass may then be dried and ground to an appropriate size. Alternatively, the co-precipitated material may be slurried and spray dried in accordance with conventional techniques. The catalyst may be extruded as pellets or formed into spears in oil as is well known in the art. For particular procedures for manufacturing the catalyst, see U.S. Pat. Nos. 5,093,299; 4,863,891 and 4,766,232, herein incorporated by reference. In one embodiment, the catalyst components may be mixed with a support in the form of the slurry followed by drying or the catalyst components may be impregnated on silica or other supports.

Bismuth may be introduced into the catalyst as an oxide or as a salt, which upon calcination will yield the oxide. The water soluble salts which are easily dispersed but form stable oxides upon heat treating are preferred. An especially preferred source for introducing bismuth is bismuth nitrate.

The iron component into the catalyst may be obtained from any compound of iron which, upon calcination will result in the oxides. As with the other elements, water soluble salts are preferred for the ease with which they may be uniformly dispersed within the catalyst. Most preferred is ferric nitrate.

The molybdenum component of the catalyst may be introduced from any molybdenum oxide such as dioxide, trioxide, pentoxide or heptaoxide. However, it is preferred that a hydrolizable or decomposable molybdenum salt be utilized as the source of the molybdenum. The most preferred starting material is ammonium heptamolybdate.

Other required components and optional promoters of the catalyst, (e.g. Ni, Co, Mg, Cr, P, Sn, Te, B, Ge, Zn, In, Ca, W, or mixtures thereof) may be derived from any suitable source. For example, cobalt, nickel and magnesium may be introduced into the catalyst using nitrate salts. Additionally, magnesium may be introduced into the catalyst as an insoluble carbonate or hydroxide which upon heat treating results in an oxide. Phosphorus may be introduced in the catalyst as an alkaline metal salt or alkaline earth metal salt or the ammonium salt but is preferably introduced as phosphoric acid.

Required and optional alkali components of the catalyst (e.g. Rb, Li, Na, K, Cs, Tl, or mixtures thereof) may be introduced into the catalyst as an oxide or as a salt, which upon calcination will yield the oxide. Preferably, salts such as nitrates which are readily available and easily soluble are used as the means of incorporating such elements into the catalyst.

The catalysts are typically prepared by mixing an aqueous solution of ammonium heptamolybdate with a silica sol to which a slurry containing the compounds, preferably nitrates of the other elements, is added. The solid material is then dried, denitrified and calcined. Preferably the catalyst is spray-dried at a temperature of between 110° C. to 350° C., preferably 110° C. to 250° C., most preferably 110° C. to 180° C. The denitrification temperature may range from 100° C. to 500° C., preferably 250° C. to 450° C. Finally, calcination takes place at a temperature of between 300° C. to 700° C., preferably between 350° C. to 650° C.

The catalysts of the instant invention are useful in ammoxidation processes for the conversion of an olefin selected from the group consisting of propylene, isobutylene or mixtures thereof, to acrylonitrile, methacrylonitrile and mixtures thereof, respectively, by reacting in the vapor phase at an elevated temperature and pressure said olefin with a molecular oxygen containing gas and ammonia in the presence of the catalyst.

Preferably, the ammoxidation reaction is performed in a fluid bed reactor although other types of reactors such as transport line reactors are envisioned. Fluid bed reactors, for the manufacture of acrylonitrile are well known in the prior art. For example, the reactor design set forth in U.S. Pat. No. 3,230,246, herein incorporated by reference, is suitable.

Conditions for the ammoxidation reaction to occur are also well known in the prior art as evidenced by U.S. Pat. Nos. 5,093,299; 4,863,891; 4,767,878 and 4,503,001; herein incorporated by reference. Typically, the ammoxidation process is performed by contacting propylene or isobutylene in the presence of ammonia and oxygen with a fluid bed catalyst at an elevated temperature to produce the acrylonitrile or methacrylonitrile. Any source of oxygen may be employed. For economic reasons, however, it is preferred to use air. The typical molar ratio of the oxygen to olefin in the feed should range from 0.5:1 to 4:1, preferably from 1:1 to 3:1.

The molar ratio of ammonia to olefin in the feed in the reaction may vary from between 0.5:1 to 2:1. There is really no upper limit for the ammonia-olefin ratio, but there is generally no reason to exceed a ratio of 2:1 for economic reasons. Suitable feed ratios for use with the catalyst of the instant invention for the production of acrylonitrile from propylene are an ammonia to propylene ratio in the range of 0.9:1 to 1.3:1, and air to propylene ratio of 8.0:1 to 12.0:1. The catalyst of the instant invention provides high yields of acrylonitrile at relatively low ammonia to propylene feed ratios of about 1:1 to about 1.05:1. These "low ammonia conditions" help to reduce unreacted ammonia in the reactor effluent, a condition known as "ammonia breakthrough", which subsequently helps to reduce process wastes. Specifically, unreacted ammonia must be removed from the reactor effluent prior to the recovery of the acrylonitrile. Unreacted ammonia is typically removed by contacting the reactor effluent with sulfuric acid to yield ammonium sulfate or by contacting the reactor effluent with acrylic acid to yield ammonium acrylate, which in both cases results in a process waste stream to be treated and/or disposed.

The reaction is carried out at a temperature of between the ranges of about 260° C. to 600° C., preferred ranges being 310° C. to 500° C., especially preferred being 350° C. to 480° C. The contact time, although not critical, is generally in the range of 0.1 to 50 seconds, with preference being to a contact time of 1 to 15 seconds.

The products of reaction may be recovered and purified by any of the methods known to those skilled in the art. One such method involves scrubbing the effluent gases from the reactor with cold water or an appropriate solvent to remove the products of the reaction and then purifying the reaction product by distillation.

The primary utility of the catalyst of the instant invention is for the ammoxidation of propylene to acrylonitrile. However, the instant catalyst may also be used for the oxidation of propylene to acrylic acid. Such processes are typically two stage processes, wherein propylene is converted in the presence of a catalyst to primarily acrolein in the first stage and the acrolein is converted in the presence of a catalyst to primarily acrylic acid in the second stage. The catalyst described herein is suitable for use in the first stage for the oxidation of propylene to acrolein.

SPECIFIC EMBODIMENTS

In order to illustrate the instant invention, catalyst of the instant invention as well as similar catalysts omitting one or more of these elements or additionally including elements detrimental to acrylonitrile production, were prepared and then evaluated under similar reaction conditions. These examples are provided for illustrative purposes only.

Catalyst Preparation

EXAMPLE 1

A catalyst of the formula 50 wt % $Cs_{0.1}K_{0.1}Ce_{0.75}Cr_{0.3}Co_{4.3}Ni_{4.4}Fe_{2.0}Bi_{0.5}Mo_{14.425}O_{57.775}$+ 50 wt % SiO2 was prepared as follows: The following metal nitrates $CsNO_3$ (1.535 g), $KNO_3$ (0.796 g), $Fe(NO_3)_3 \cdot 9H_2O$ (63.643 g), $Ni(NO_3)_2 \cdot 6H_2O$ (100.778 g), $Co(NO_3)_2 \cdot 6H_2O$ (98.572 g), $Bi(NO_3)_3 \cdot 5H_2O$ (19.104 g), and $(NH_4)_2Ce(NO_3)_6$ (64.773 g of a 50% solution) were melted together at ~70° C. in a 1000 ml beaker. Ammonium heptamolybdate (AHM) (200.603 g) was dissolved in 310 ml of distilled water. To this solution $CrO_3$ (2.363 g) dissolved in a 20 ml water was added. Then the silica (625 g of a 40% $SiO_2$ sol) was added followed by the metal nitrates melt. The resulted yellow slurry was then spray dried. The obtained material was denitrified at 290° C./3 hours and 425° C. for 3 hours and then was calcined at 570° C. for 3 hours, in air.

EXAMPLE 2

Using the preparation described in Example 1 above, a catalyst of the formula 50 wt % $Cs_{0.1}K_{0.1}Li_{0.3}Ce_{0.58}Cr_{0.12}Co_{5.3}Ni_{3.1}Fe_{1.8}Bi_{0.62}Mo_{13.744}O_{54.852}$+50 wt % SiO2 was prepared as follows: The following metal nitrates $CsNO_3$ (12.877 g), $KNO_3$ (6.679 g), $LiNO_3$ (13.665 g), $Fe(NO_3)_3 \cdot 9H_2O$ (480.431 g), $Ni(NO_3)_2 \cdot 6H_2O$ (595.542 g), $Co(NO_3)_2 \cdot 6H_2O$ (1019.059 g), $Bi(NO_3)_3 \cdot 5H_2O$ (198.691 g), and $(NH_4)_2Ce(NO_3)_6$ (420.146 g of a 50% solution) were melted together at ~70° C. in a 1000 ml beaker. Ammonium heptamolybdate (AHM) (1603.142 g) was dissolved in 1760 ml of distilled water. To this solution $CrO_3$ (7.928 g) dissolved in a 20 ml water was added. Then the silica (5000 g of a 40% $SiO_2$ sol) was added followed by the metal nitrates melt. The resulted yellow slurry was then spray dried. The obtained material was denitrified at 290° C./3 hours and 425° C. for 3 hours and then was calcined at 570° C. for 3 hours, in air.

Comparative Example A (no Ni)

Using the preparation described in Example 1 above, a catalyst of the formula 50 wt % $Cs_{0.1}K_{0.1}Ce_{0.75}Cr_{0.3}Co_{8.7}Fe_{2.0}Bi_{0.5}Mo_{14.425}O_{57.775}$+50 wt % SiO2 was prepared as per the following recipe: $CsNO_3$ (1.535 g), $KNO_3$ (0.796 g), $Fe(NO_3)_3 \cdot 9H_2O$ (63.623 g), $Co(NO_3)_2 \cdot 6H_2O$ (199.375 g), $Bi(NO_3)_3 \cdot 5H_2O$ (19.098 g), and $(NH_4)_2Ce(NO_3)_6$ (64.753 g of a 50% solution) were melted together at ~70° C. in a 1000 ml beaker. Ammonium heptamolybdate (AHM)(200.603 g) was dissolved in 310 ml of distilled water. To this solution $CrO_3$ (2.362 g) dissolved in a 20 ml water was added. Then the silica (625 g of a 40% $SiO_2$ sol) was added followed by the metal nitrates melt.

Comparative Example B (no K)

Using the preparation described in Example 1 above, a catalyst of the formula 50 wt % $Cs_{0.2}Ce_{0.75}Cr_{0.3}Co_{4.3}Ni_{4.4}Fe_{2.0}Bi_{0.5}Mo_{14.425}O_{57.775}$+50 wt % $SiO2$ was prepared per the following recipe: $CsNO_3$ (3.061 g), $Fe(NO_3)_3.9H_2O$ (63.456 g), $Ni(NO_3)_2.6H_2O$ (100.481 g), $Co(NO_3)_2.6H_2O$ (98.282 g), $Bi(NO_3)_3.5H_2O$ (19.047 g), and $(NH_4)_2Ce(NO_3)_6$ (64.582 g of a 50% solution) were melted together at ~70° C. in a 1000 ml beaker. Ammonium heptamolybdate (AHM)(200.603 g) was dissolved in 310 ml of distilled water. To this solution $CrO_3$ (2.356 g) dissolved in a 20 ml water was added. Then the silica (625 g of a 40% $SiO_2$ sol) was added followed by the metal nitrates melt.

Comparative Example C (with Mn)

Using the preparation described in Example 1 above, a catalyst of the formula 50 wt % $Cs_{0.1}K_{0.1}Ce_{0.75}Cr_{0.3}Co_{4.3}Ni_{4.4}Mn_{0.5}Fe_{2.0}Bi_{0.5}Mo_{14.425}O_{57.775}$+50 wt % $SiO2$ was prepared per the following recipe: $CsNO_3$ (1.485 g), $KNO_3$ (0.77 g), $Fe(NO_3)_3.9H_2O$ (61.559 g), $Ni(NO_3)_2.6H_2O$ (97.478 g), $Co(NO_3)_2.6H_2O$ (95.345 g), $Mn(NO_3)_2$.(13.34 g of a 51.1% solution) $Bi(NO_3)_3.5H_2O$ (18.478 g), and $(NH_4)_2Ce(NO_3)_6$ (62.653 g of a 50% solution) were melted together at ~70° C. in a 1000 ml beaker. Ammonium heptamolybdate (AHM)(200.761 g) was dissolved in 310 ml of distilled water. To this solution $CrO_3$ (2.286 g) dissolved in a 20 ml water was added. Then the silica (625 g of a 40% $SiO_2$ sol) was added followed by the metal nitrates melt.

Comparative Example D (with Zn)

Using the preparation described in Example 1 above, a catalyst of the formula 50 wt % $Cs_{0.1}K_{0.1}Ce_{0.75}Cr_{0.3}Co_{4.3}Ni_{2.2}Zn_{2.0}Fe_{2.0}Bi_{0.5}Mo_{14.425}O_{57.775}$+50 wt % $SiO2$ was prepared per the following recipe: $CsNO_3$ (1.55 g), $KNO_3$ (0.804 g), $Fe(NO_3)_3.9H_2O$ (64.244 g), $Ni(NO_3)_2.6H_2O$ (50.865 g), $Co(NO_3)_2.6H_2O$ (99.503 g), $Zn(NO_3)_2.6H_2O$ (47.301 g), $Bi(NO_3)_3.5H_2O$ (19.284 g), and $(NH_4)_2Ce(NO_3)_6$ (65.385 g of a 50% solution) were melted together at ~70° C. in a 1000 ml beaker. Ammonium heptamolybdate (AHM)(199.759 g) was dissolved in 310 ml of distilled water. To this solution $CrO_3$ (2.385 g) dissolved in a 20 ml water was added. Then the silica (625 g of a 40% $SiO_2$ sol) was added followed by the metal nitrates melt.

Catalyst Testing

All testing was conducted in a 40 cc fluid bed reactor. Propylene was feed into the reactor at a rate of 0.06 WWH (i.e. weight of propylene/weight of catalyst/hour). Pressure inside the reactor was maintained at 10 psig. Reaction temperature was 430° C. After a stabilization period of ~20 hours samples of reaction products were collected. Reactor effluent was collected in bubble-type scrubbers containing cold HCl solution. Off-gas rate was measured with soap film meter, and the off-gas composition was determined at the end of the run with the aid of gas chromatograph fitted with a split column gas analyzer. At the end of the recovery run, the entire scrubber liquid was diluted to approximately 200 gms with distilled water. A weighted amount of 2-butanone was used as internal standard in a ~50 gram aliquot of the dilute solution. A 2 μl sample was analyzed in a GC fitted with a flame ionization detector and a Carbowax column. The amount of $NH_3$ was determined by titrating the free HCl excess with NaOH solution. The following examples are illustrative of our invention.

TABLE 1

| Example | Active Phase Composition | Total $C_3^=$ Conv. | Conv. to AN | Sel. to AN |
|---|---|---|---|---|
| 1 | $Cs_{0.1}K_{0.1}Ce_{0.75}Cr_{0.3}Co_{4.3}Ni_{4.4}Fe_{2.0}Bi_{0.5}Mo_{14.425}O_{57.775}$ | 98.5 | 82.6 | 83.9 |
| 2 | $Cs_{0.1}K_{0.1}Li_{0.3}Ce_{0.58}Cr_{0.12}Co_{5.3}Ni_{3.1}Fe_{1.8}Bi_{0.62}Mo_{13.744}O_{54.852}$ | 98.8 | 81.9 | 82.9 |
| A | $Cs_{0.1}K_{0.1}Ce_{0.75}Cr_{0.3}Co_{8.7}Fe_{2.0}Bi_{0.5}Mo_{14.425}O_{57.775}$ | 95.8 | 80.6 | 84.4 |
| B | $Cs_{0.2}Ce_{0.75}Cr_{0.3}Co_{4.3}Ni_{4.4}Fe_{2.0}Bi_{0.5}Mo_{14.425}O_{57.775}$ | 96.6 | 80.5 | 83.3 |
| C | $Cs_{0.1}K_{0.1}Ce_{0.75}Cr_{0.3}Co_{4.3}Ni_{4.4}Mn_{0.5}Fe_{2.0}Bi_{0.5}Mo_{14.425}O_{57.775}$ | 99.4 | 81.6 | 82.0 |
| D | $Cs_{0.1}K_{0.1}Ce_{0.75}Cr_{0.3}Co_{4.3}Ni_{2.2}Zn_{2.0}Fe_{2.0}Bi_{0.5}Mo_{14.425}O_{57.775}$ | 96.4 | 81.0 | 84.0 |

Notes:
1. All test catalyst compositions contained 50% active phase and 50% $SiO_2$.
2. "Total $C_3^=$ Conv." is the mole percent per pass conversion of propylene to all products.
3. "Conv. to AN" is the mole percent per pass conversion of propylene to acrylonitrile.
4. "Sel. to AN" is the ratio of moles of acrylonitrile produced to moles of propylene converted expressed in percent.

EXAMPLE 3

Using preparation methods similar to that described in Example 2 above, several catalyst (50% active phase and 50% $SiO_2$) additionally comprising lithium were prepared. The active phase compositions were as follows:

$Cs_{0.1}K_{0.1}Li_{0.3}Ce_{1.0}Cr_{0.12}Co_{5.3}Ni_{3.1}Fe_{1.8}Bi_{0.62}Mo_{14.44}O_{57.78}$ $Cs_{0.1}K_{0.1}Li_{0.3}Ce_{0.8}Cr_{0.12}Co_{5.3}Ni_{3.1}Fe_{1.8}Bi_{0.62}Mo_{14.074}O_{56.282}$ $Cs_{0.1}K_{0.1}Li_{0.3}Ce_{0.8}Cr_{0.12}Co_{4.2}Ni_{4.2}Fe_{1.8}Bi_{0.62}Mo_{14.074}O_{56.282}$ $Cs_{0.1}K_{0.1}Li_{0.3}Ce_{1.0}Cr_{0.12}Co_{1.0}Ni_{7.4}Fe_{1.8}Bi_{0.62}Mo_{14.374}O_{57.532}$ $Cs_{0.1}K_{0.1}Li_{0.3}Ce_{1.0}Cr_{0.12}Co_{5.3}Ni_{3.1}Fe_{1.8}Bi_{0.62}Mo_{14.074}O_{57.582}$ $Cs_{0.1}K_{0.1}Li_{0.3}Ce_{0.8}Cr_{0.5}Co_{5.3}Ni_{3.1}Fe_{1.8}Bi_{0.62}Mo_{13.969}O_{55.862}$ $Cs_{0.1}K_{0.1}Li_{0.3}Na_{0.2}Ce_{1.0}Cr_{0.12}Co_{1.0}Ni_{7.4}Fe_{1.8}Bi_{0.62}Mo_{14.374}O_{57.982}$ $Cs_{0.1}K_{0.1}Li_{0.1}Ce_{1.0}Cr_{0.12}Co_{4.2}Ni_{4.2}Fe_{1.8}Bi_{0.62}Mo_{14.26}O_{57.14}$ $Cs_{0.1}K_{0.1}Li_{0.3}Ce_{1.0}Cr_{0.12}Co_{4.2}Ni_{4.2}Fe_{1.8}Bi_{0.62}Mo_{14.16}O_{56.94}$ $Cs_{0.1}K_{0.1}Li_{0.3}Na_{0.2}Ce_{0.8}Cr_{0.12}Co_{4.2}Ni_{4.2}Fe_{1.8}Bi_{0.62}Mo_{14.16}O_{56.64}$ $Cs_{0.1}K_{0.1}Li_{0.1}Ce_{1.0}Cr_{0.12}Co_{2.0}Ni_{5.0}Fe_{1.8}Bi_{0.62}Mo_{12.86}O_{51.54}$ $Cs_{0.1}K_{0.1}Li_{0.1}Ce_{1.0}Cr_{0.12}Co_{3.2}Ni_{4.2}Fe_{2.0}Bi_{0.62}Mo_{14.26}O_{54.04}$ $Cs_{0.1}K_{0.1}Li_{0.1}Na_{0.2}Ce_{1.0}Cr_{0.12}Co_{4.2}Ni_{4.2}Fe_{1.8}Bi_{0.62}Mo_{14.36}O_{57.54}$ $Cs_{0.1}K_{0.1}Li_{0.3}Ce_{0.8}Cr_{0.12}Co_{4.2}Ni_{4.2}Fe_{2.2}Bi_{0.62}Mo_{14.76}O_{59.34}$

The above catalyst compositions were tested as described above. The overall conversion to nitrites (i.e. mole percent per pass conversion of propylene to acrylonitrile, acetonitrile and hydrogen cyanide) for the above catalysts typically was in the range of about 86% to about 88%.

The catalyst composition of the instant invention is unique in that it comprises potassium, cesium, cerium, chromium, cobalt, nickel, iron, bismuth, and molybdenum, in the substantial absence of manganese and zinc. This combination of elements in the relative proportions described herein have not previously utilized in a single ammoxidation catalyst formulation. As illustrated in Table 1, for the ammoxidation of propylene to acrylonitrile, a catalyst of the instant invention has exhibited better performance than catalysts comprising similar (but not exact) combinations of elements found in prior art patents. More specifically, a catalyst containing comprising potassium, cesium, cerium, chromium, cobalt, nickel, iron, bismuth, and molybdenum in the substantial absence of manganese or zinc, showed higher overall conversion and higher conversions to acrylonitrile when propylene was ammoxidized over such catalyst at elevated temperatures in the presence of ammonia and air compared to similar catalysts falling outside the scope of the instant invention.

While the foregoing description and the above embodiments are typical for the practice of the instant invention, it is evident that many alternatives, modifications, and variations will be apparent to those skilled in the art in light of this description. Accordingly, it is intended that all such alternatives, modifications and variations are embraced by and fall within the spirit and broad scope of the appended claims.

The claimed invention is:

1. A catalyst composition comprising a complex of catalytic oxides comprising potassium, cesium, cerium, chromium, cobalt, nickel, iron, bismuth, and molybdenum, wherein the relative ratios of these elements are represented by the following general formula $A_aK_bCs_cCe_dCr_eCo_fNi_gX_hFe_iBi_jMo_{12}O_x$ wherein
A is Rb, Na, Li, Tl, or mixtures thereof,
X is P, Sb, Te, B, Ge, W, Ca, Mg, a rare earth element, or mixtures thereof,
a is 0 to about 1,
b is about 0.01 to about 1,
c is about 0.01 to about 1,
d is about 0.01 to about 3,
e is about 0.01 to about 2,
f is about 0.01 to about 10,
g is about 0.1 to about 10,
h is 0 to about 4,
i is about 0.1 to about 4,
j is about 0.05 to about 4,
x is a number determined by the valence requirements of the other elements present,
and wherein the catalyst is substantially free of manganese and zinc.

2. The catalyst composition of claim 1, wherein the catalyst comprises phosphorus.

3. The catalyst composition of claim 1, wherein the catalyst comprises magnesium.

4. The catalyst composition of claim 1, wherein the catalyst is substantially free of magnesium.

5. The catalyst composition of claim 1, wherein the catalyst comprises rubidium.

6. The catalyst composition of claim 1, wherein the catalyst comprises lithium.

7. The catalyst composition of claim 1, wherein f+g is about 4 to about 10.

8. The catalyst composition of claim 1, wherein the catalyst composition comprises a support selected from the group consisting of silica, alumina, zirconium, titania, or mixtures thereof.

9. The catalyst composition of claim 8, wherein the support comprises between 30 and 70 weight percent of the catalyst.

10. The catalyst composition of claim 1, wherein the catalyst composition comprises silica having an average colloidal particle size in between about 8 nm and about 100 nm.

11. A catalyst composition comprising a complex of catalytic oxides comprising potassium, cesium, cerium, chromium, cobalt, nickel, iron, bismuth, and molybdenum, wherein the relative ratios of these elements are represented by the following general formula $A_aLi_{a'}K_bCs_cCe_dCr_eCo_fNi_gX_hFe_iBi_jMo_{12}O_x$ wherein A is Rb, Na, Tl, or mixtures thereof,
X is P, Sb, Te, B, Ge, W, Ca, Mg, a rare earth element, or mixtures thereof,
a is 0 to about 1,
a' is about 0.01 to about 1,
b is about 0.01 to about 1,
c is about 0.01 to about 1,
d is about 0.01 to about 3,
e is about 0.01 to about 2,
f is about 0.01 to about 10,
g is about 0.1 to about 10,
h is 0 to about 4,
i is about 0.1 to about 4,
j is about 0.05 to about 4,
x is a number determined by the valence requirements of the other elements present,
and wherein the catalyst is substantially free of manganese and zinc.

12. The catalyst composition of claim 11, wherein f+g is about 4 to about 10.

13. A process for the conversion of an olefin selected from the group consisting of propylene, isobutylene or mixtures thereof, to acrylonitrile, methacrylonitrile, and mixtures thereof, respectively, by reacting in the vapor phase at an elevated temperature and pressure said olefin with a molecular oxygen containing gas and ammonia in the presence of a catalyst comprising a complex of catalytic oxides, comprising potassium, cesium, cerium, chromium, cobalt, nickel, iron, bismuth, molybdenum, wherein the relative ratios of these elements are represented by the following general formula $A_aK_bCs_cCe_dCr_eCo_fNi_gX_hFe_iBi_jMo_{12}O_x$ wherein
- A is Rb, Na, Li, Tl, or mixtures thereof,
- X is P, Sb, Te, B, Ge, W, Ca, Mg, a rare earth element, or mixtures thereof,
- a is 0 to about 1,
- b is about 0.01 to about 1,
- c is about 0.01 to about 1,
- d is about 0.01 to about 3,
- e is about 0.01 to about 2,
- f is about 0.01 to about 10,
- g is about 0.1 to about 10,
- h is 0 to about 4,
- i is about 0.1 to about 4,
- j is about 0.05 to about 4,
- x is a number determined by the valence requirements of the other elements present, and wherein the catalyst is substantially free of manganese and zinc.

14. The process of claim 13, wherein the catalyst comprises phosphorus.

15. The process of claim 13, wherein the catalyst comprises magnesium.

16. The process of claim 13, wherein the catalyst comprises rubidium.

17. The process of claim 13, wherein the catalyst comprises lithium.

18. The process of claim 13, wherein, in the catalyst composition, f+g is about 4 to about 10.

19. The process of claim 13, wherein the catalyst composition comprises a support selected from the group consisting of silica, alumina, zirconium, titania, or mixtures thereof.

20. The process of claim 19, wherein the support comprises between 30 and 70 weight percent of the catalyst.

21. The process of claim 13, wherein the catalyst composition comprises silica having an average colloidal particle size in between about 8 nm and about 100 nm.

* * * * *